United States Patent [19]

Korthoff et al.

[11] Patent Number: 4,522,327
[45] Date of Patent: Jun. 11, 1985

[54] SURGICAL FASTENER APPLYING APPARATUS

[75] Inventors: Herbert W. Korthoff, Wilton; Thomas M. Tompkins, Trumbull, both of Conn.

[73] Assignee: United States Surgical Corporation, Norwalk, Conn.

[21] Appl. No.: 495,828

[22] Filed: May 18, 1983

[51] Int. Cl.³ .............................................. A61B 17/04
[52] U.S. Cl. ................................. 227/19; 128/334 R; 227/DIG. 1
[58] Field of Search ............... 128/334 R, 334 C, 335; 227/DIG. 1, 19, 83, 156

[56] References Cited

U.S. PATENT DOCUMENTS

| | | | |
|---|---|---|---|
| 2,344,071 | 3/1944 | Wilson et al. | 227/DIG. 1 |
| 3,017,637 | 1/1962 | Sampson | 227/DIG. 1 |
| 3,078,465 | 2/1963 | Bobrov | 227/DIG. 1 |
| 3,079,606 | 3/1963 | Bobrov et al. | 227/DIG. 1 |
| 3,080,564 | 3/1963 | Strekopitov et al. | 227/DIG. 1 |
| 3,269,630 | 8/1966 | Fleischer | 227/107 |
| 3,269,631 | 8/1966 | Takaro | 227/144 |
| 3,275,211 | 9/1966 | Hirsch et al. | 227/124 |
| 3,499,591 | 3/1970 | Green | 227/76 |
| 3,551,987 | 1/1971 | Wilkinson | 29/212 |
| 3,935,981 | 2/1976 | Akopov et al. | 227/19 |
| 4,111,206 | 9/1978 | Vishnevsky et al. | 128/305 |
| 4,241,861 | 12/1980 | Fleischer | 227/135 |
| 4,272,002 | 6/1981 | Moshofsky | 227/19 |
| 4,354,628 | 10/1982 | Green | 227/19 |
| 4,383,634 | 5/1983 | Green | 227/19 |
| 4,402,444 | 9/1983 | Green | 227/19 |
| 4,402,445 | 9/1983 | Green | 227/19 |

FOREIGN PATENT DOCUMENTS

406832 12/1924 Fed. Rep. of Germany.
869388 3/1953 Fed. Rep. of Germany.

Primary Examiner—Paul A. Bell
Attorney, Agent, or Firm—Robert R. Jackson; John E. Nathan

[57] ABSTRACT

A surgical fastener holding assembly for use in surgical fastener applying apparatus is removably mounted relative to the remainder of the apparatus by mounting means which allows the fastener holding assembly to both translate and pivot toward the associated anvil member.

30 Claims, 12 Drawing Figures

SURGICAL FASTENER APPLYING APPARATUS

BACKGROUND OF THE INVENTION

This invention relates to surgical fastener applying apparatus, and more particularly to apparatus for applying a plurality of surgical fasteners, such as surgical staples, in a longitudinal array.

Apparatus for applying a plurality of surgical fasteners in a longitudinal array is now well known. In some apparatus of this type, such as the apparatus shown in Hirsch et al. U.S. Pat. No. 3,275,211, the fastener holding assembly reciprocates or translates along a straight line toward or away from an opposing anvil member. In other apparatus of this type, such as the apparatus shown in Green U.S. Pat. No. 4,354,628, the fastener holding assembly essentially pivots toward or away from the opposing anvil member. For convenience herein, apparatus of the type illustrated by the Hirsch et al. patent will be referred to as "reciprocating fastener applying apparatus", while the other apparatus, typified by the Green patent, will be referred to as "pivoting fastener applying apparatus". (It should be noted that a limited amount of reciprocal motion is permitted in the apparatus shown in the Green patent by virtue of the elongated apertures which form one part of the pivotal connection between the fastener holding assembly and the anvil member.) In both of these prior art devices, at least the fastener holding assembly is preferably disposable after a single use because this completely avoids all difficulty, expense, and delay which would otherwise be occasioned by the need to clean, sterilize, and reload the fastener holding assembly for reuse.

Pivoting fastener applying apparatus has the advantage that the pivotal connection between the fastener holding assembly and the anvil member serves to assure that these two components of the system are properly aligned. Such alignment is necessary so that the anvil member will operate properly to complete the fasteners driven from the fastener holding assembly. For example, if the fasteners are metal surgical staples, depressions in the anvil member must line up with the staple legs in order to properly crimp the staples. Alternatively, if the fasteners are two-part interlocking fasteners, such as are shown in Noiles U.S. Pat. No. 4,060,089, then the retainer parts of these fasteners, which are carried by the anvil member, must line up properly with the fastener parts carried by the fastener holding assembly in order for the two parts of each fastener to interlock.

One possible advantage of reciprocating surgical fastener applying apparatus is that such apparatus may be somewhat less prone to squeeze the tissue out of the apparatus as the fastener holding assembly moves toward the anvil member in order to clamp the tissue in preparation for fastening.

In view of the foregoing, it is an object of this invention to provide surgical fastener applying apparatus having all the advantages of the above-described reciprocating and pivoting fastener applying apparatus.

It is another object of this invention to improve and simplify surgical fastener applying apparatus.

SUMMARY OF THE INVENTION

These and other objects of the invention are accomplished in accordance with the principles of the invention by surgical fastener applying apparatus in which the fastener holding assembly is able to both reciprocate and pivot toward the anvil member. The fastener holding assembly is separable from the anvil member. When tissue is to be fastened, the fastener holding assembly is positioned on a first pin which extends perpendicular to the anvil member at one end of that member. The connection between the first pin and the fastener holding assembly is relatively loose. This connection orients the fastener holding assembly relative to the anvil member and provides approximate alignment between these elements. This connection also both guides reciprocal motion of the fastener holding assembly toward the anvil member and permits pivotal motion of the fastener holding assembly toward the anvil member. A spring is preferably provided adjacent the first pin to resiliently bias the fastener holding assembly away from the anvil member at that point.

After the fastener holding assembly has been positioned relative to the first pin, the tissue to be fastened is located between the fastener holding assembly and the anvil member. The fastener holding assembly is then pushed toward the anvil member, preferably by means of a clamping force applied to the fastener holding assembly along an axis parallel to the first pin but intermediate the longitudinal axis of the first pin and the opposite end of the fastener holding assembly. This causes the end of the fastener holding assembly which is remote from the first pin to pivot toward the anvil member, thereby closing off the side of the apparatus which is not already closed by the presence of the first pin. The tissue to be fastened is thus substantially prevented from escaping from the apparatus during further clamping of the tissue.

Continued application of the clamping force to the fastener holding assembly now causes that assembly to pivot in the opposite direction, thereby causing the fastener holding assembly to move along the first pin. When the fastener holding assembly is substantially parallel to the anvil member, a precision pivotal connection is formed between a second pin, which is fixedly mounted relative to the anvil member and which has a longitudinal axis perpendicular to the plane defined by the longitudinal axes of the anvil member and the fastener holding member, and the base of a U- or V-shaped yoke structure, which is mounted on the fastener holding assembly and which opens toward the anvil member. This precision pivotal connection provides the necessary precise alignment between the fastener holding assembly and the anvil member.

If for any reason the fastener holding assembly does not contact the anvil member on the side of the apparatus opposite the first pin before the precise pivotal connection including the second pin is formed, then the final motion of the fastener holding assembly prior to fastening the tissue will be pivoting of the fastener holding assembly about the second pin.

Proper alignment of the anvil member and the fastener holding assembly is preferably further assured by a third pin parallel to the first pin and extending between the anvil member and the fastener holding assembly on the side of the apparatus remote from the first pin.

After the fastener holding assembly and anvil member are positioned relative to one another as outlined above, the fastener holding assembly is operated to drive the fasteners through the tissue. The clamping force on the fastener holding assembly is then released to open the apparatus, and the fastened tissue is removed.

Further features of the invention, its nature and various advantages will be more apparent from the accompanying drawing and the following detailed description of the invention.

BRIEF DESCRIPTION OF THE DRAWING

FIGS. 7 and 8 are enlarged elevational sectional views of a portion of the apparatus of FIGS. 1–6 showing successive stages in the operation of that apparatus. FIG. 7 corresponds to the operating stage shown in FIG. 5, and FIG. 8 corresponds to the operating stage shown in FIG. 6.

DETAILED DESCRIPTION OF THE INVENTION

Figure 1:
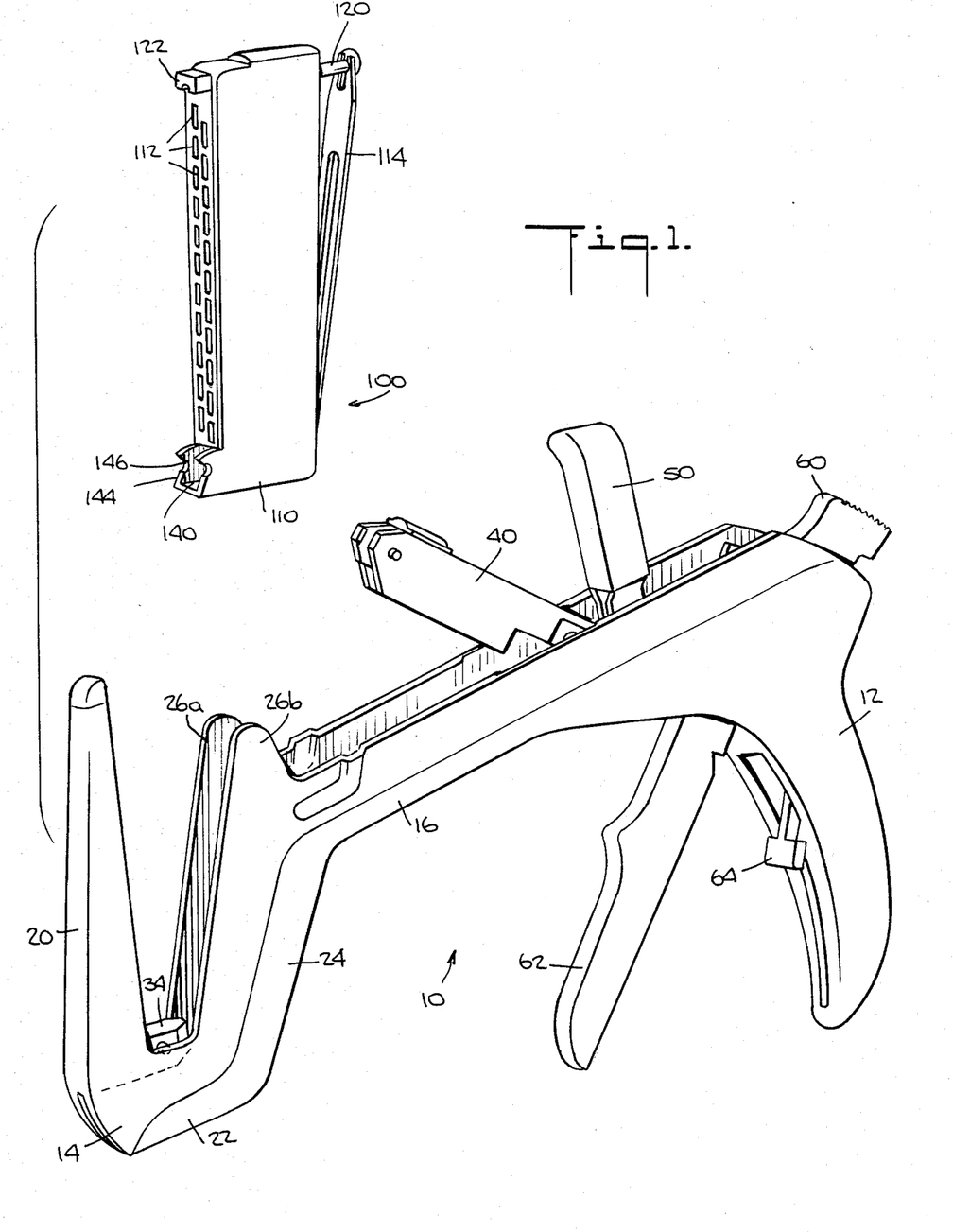
FIG. 1 is a perspective view of a preferred embodiment of the invention with the preferably disposable fastener holding assembly removed from the preferably reusable actuator.

The two principal components of a preferred embodiment of the invention are shown separately in FIG. 1. These two components are actuator 10 and fastener holding assembly 100. Many of the details of the construction and operation of actuator 10, especially the portion to the right of U-shaped portion 14 as viewed in FIG. 1, are not necessary to an understanding of the present invention. This right-hand portion of actuator 10 will therefore be described only briefly herein. Additional details regarding this portion of the actuator will be found in commonly assigned, co-pending Green U.S. patent application Ser. No. 267,080, filed May 26, 1981.

Figure 8:
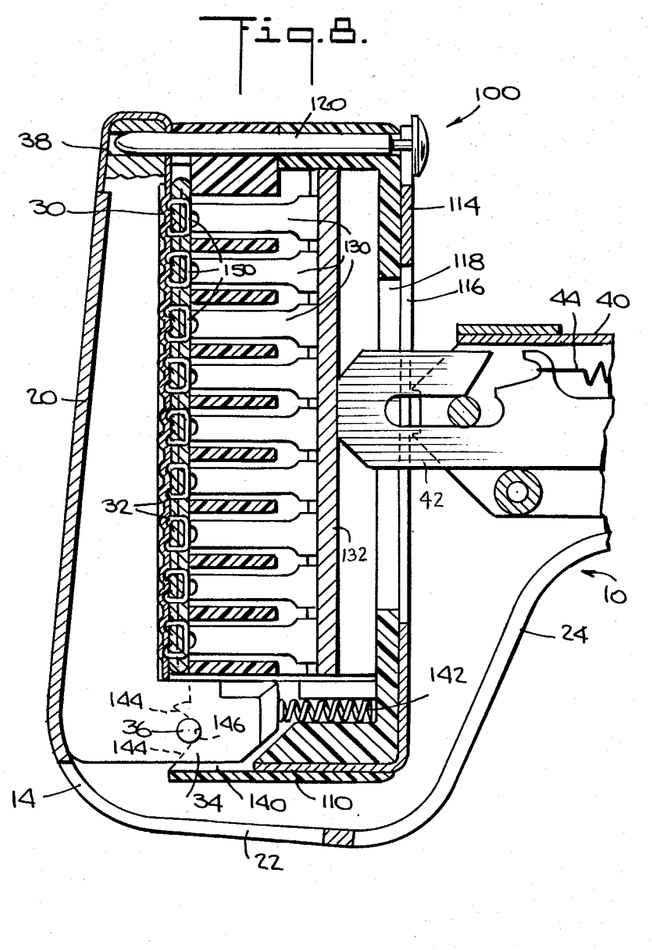

Actuator 10 includes proximal handle 12, distal U-shaped portion 14, and intermediate shaft assembly 16. U-shaped portion 14 has a distal leg 20, a base 22, and a proximal leg 24. The proximal-facing surface of distal leg 20 is an anvil member 30 (FIG. 9) having two parallel rows of staple-clinching pockets or depressions 32. During operation of the apparatus, each pocket 32 receives the distal end of one of the two legs of a metal surgical staple driven from fastener holding assembly 100. Each pocket 32 bends the staple leg it receives so that all the staples are clinched and the tissue is thereby fastened as best seen in FIG. 8.

The proximal leg 24 of the U-shaped portion of actuator 10 comprises two parallel, laterally spaced side plates 26a and 26b (collectively referred to as plates 26). The spacing between plates 26 is great enough so that fastener holding assembly 100 slides easily into and out of that space, but small enough so that plates 26 provide lateral guidance for fastener holding assembly 100 during operation of the apparatus as described below.

Figures 3, 9:
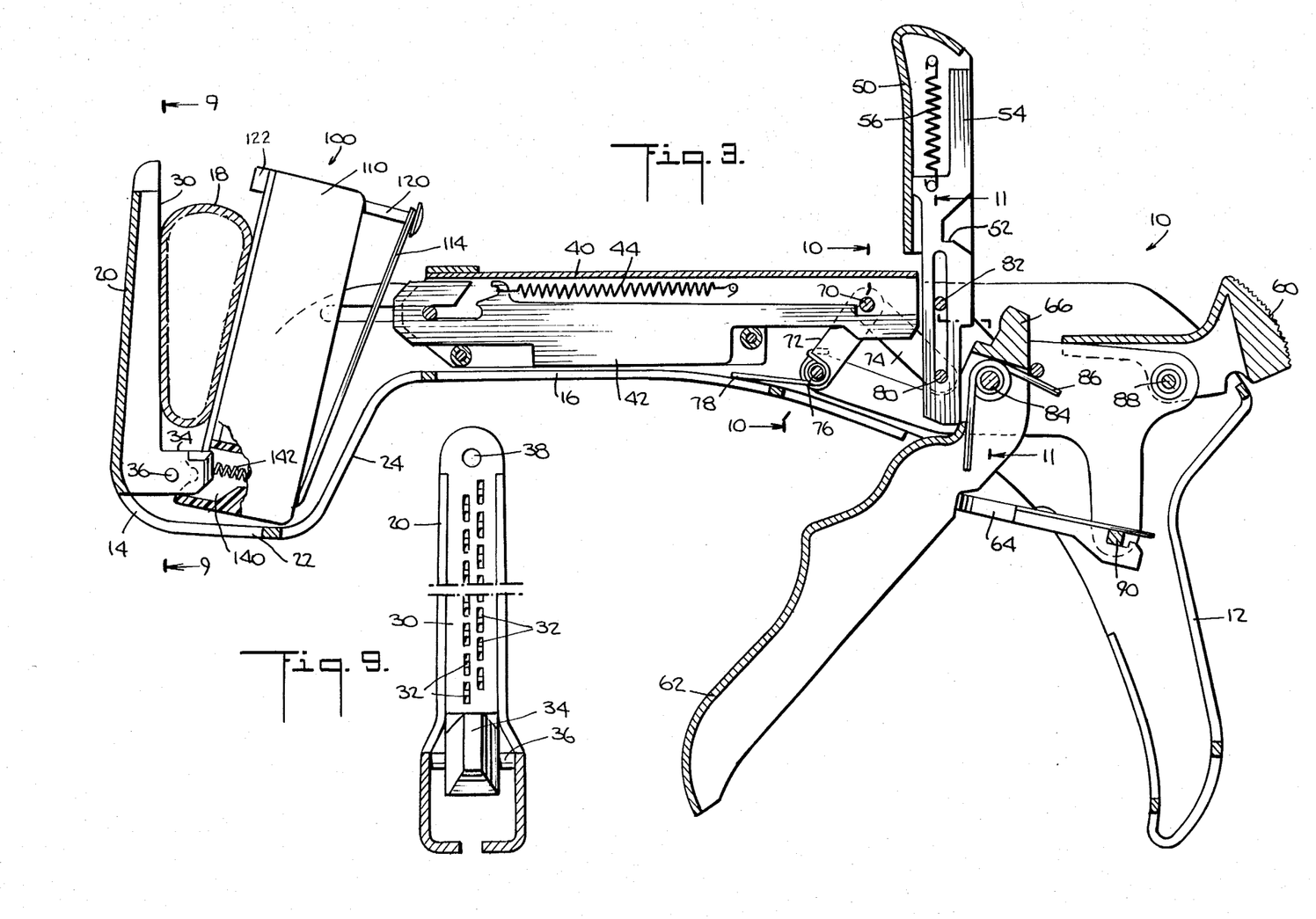
FIGS. 3–6 are a series of elevational sectional views of the apparatus of FIGS. 1 and 2 showing successive stages in the operation of that apparatus.
FIGS. 9–11 are sectional views taken respectively along the lines 9—9, 10—10, and 11—11 in FIG. 3.
Figure 7:
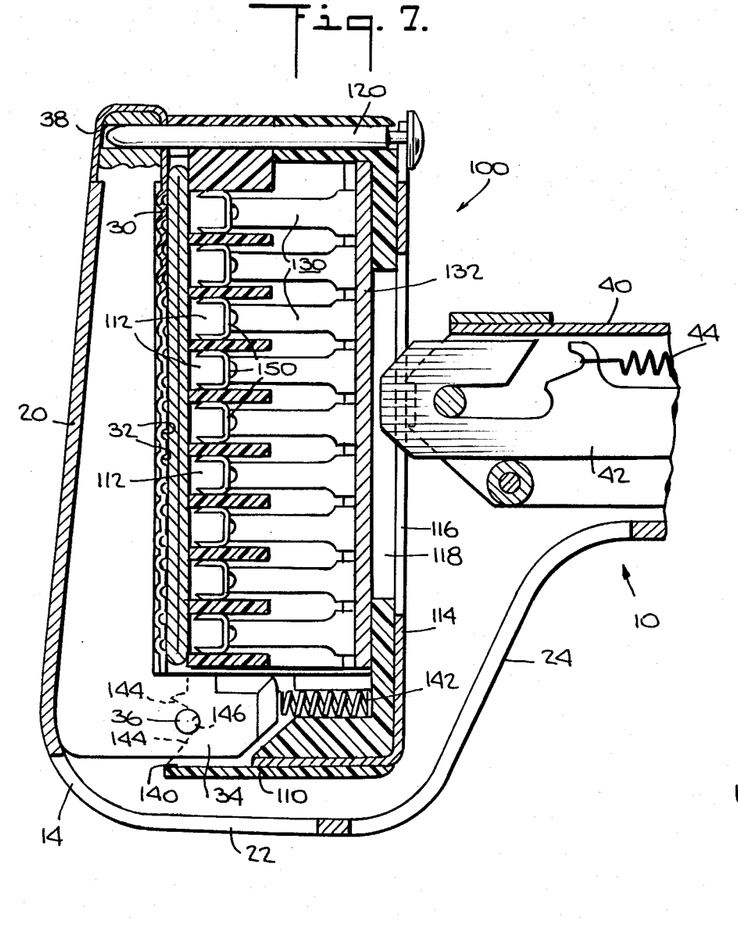

Near the base 22 of the U-shaped portion of actuator 10 is a pin 34 which is fixedly mounted relative to anvil member 30 and which extends in the proximal direction substantially perpendicular to the anvil member. As best seen in FIGS. 3, 7, and 8, pin 34 is designed to fit into aperture 140 near the bottom of the distal side of fastener holding assembly 100. When fastener holding assembly 100 is dropped into actuator 10 between plates 26, plates 26 guide aperture 140 toward the proximal end of pin 34. A compression coil spring 142, which is part of assembly 100 and which extends distally into aperture 140, contacts the proximal end of pin 34 and initially keeps at least the lower portion of assembly 100 spaced from anvil member 30.

Figure 2:
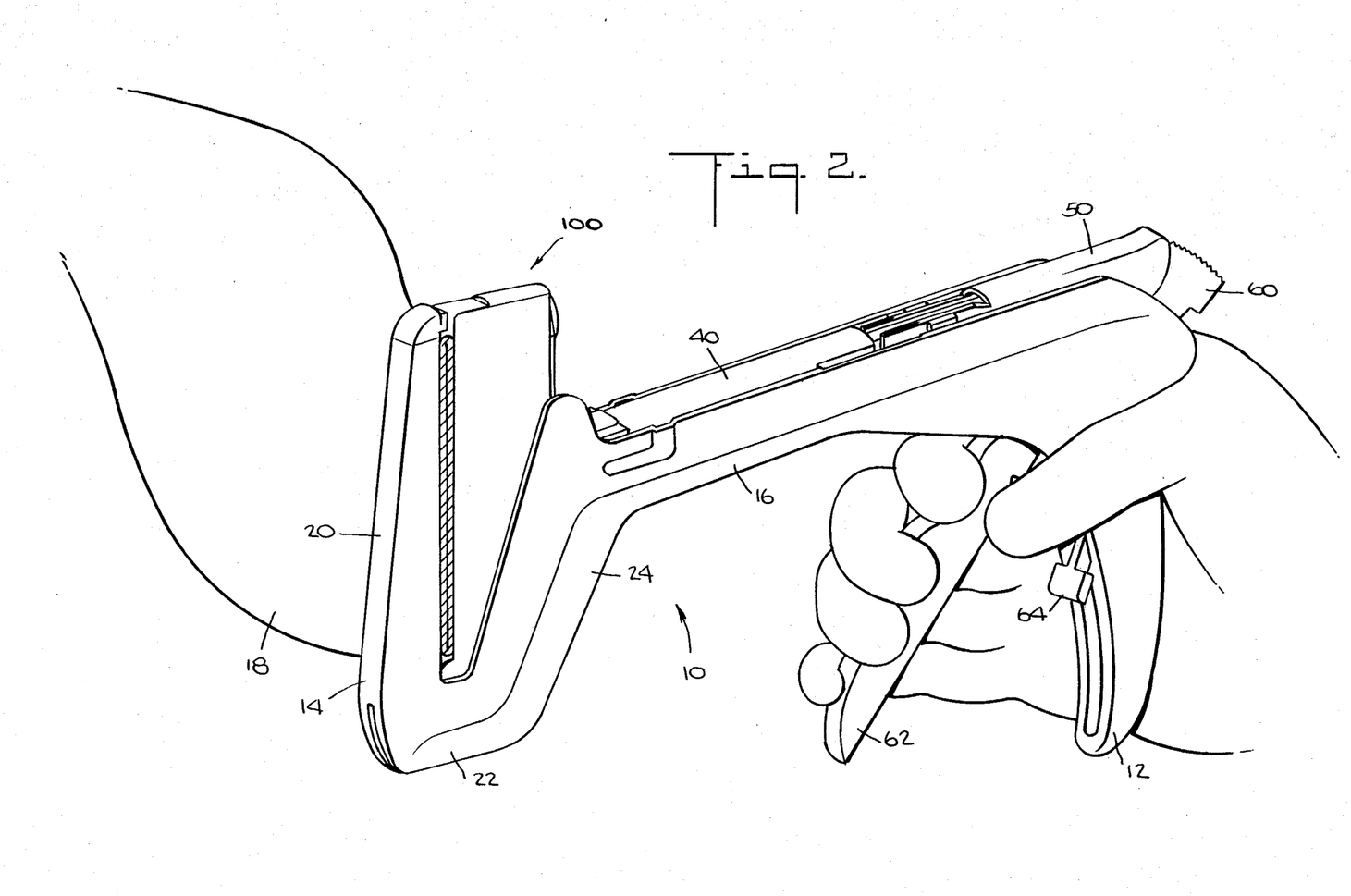
FIG. 2 is another perspective view of the apparatus of FIG. 1 showing the parts of that apparatus assembled and in use.

Continuing now with the discussion of actuator 10, clamping assembly 40 is mounted for both pivotal and reciprocal motion relative to the actuator frame. In FIG. 1, clamping assembly 40 is shown retracted in the proximal direction and pivoted out from the actuator frame. In FIG. 2, clamping assembly 40 is shown pivoted parallel to the actuator frame and extended in the distal direction in order to apply clamping force to the proximal side of fastener holding assembly 100 and to thereby clamp the tissue to be fastened between anvil member 30 and fastener holding assembly 100. The motion of fastener holding assembly 100 in response to clamping assembly 40 will be described in detail after the remainder of actuator 10 has been discussed.

Clamping assembly 40 is pivoted by manual operation, but it is reciprocated by clamp actuator 50. Clamp actuator 50 is also pivotally mounted on actuator 10. In FIG. 1, clamp actuator 50 is shown pivoted out from actuator 10, which corresponds to the proximally retracted position of clamping assembly 40. In FIG. 2, clamp actuator 50 is shown pivoted parallel to actuator 10, which causes clamping assembly 40 to translate in the distal direction as shown in that Figure. Clamp actuator 50 is pivoted manually.

Figures 5, 12:
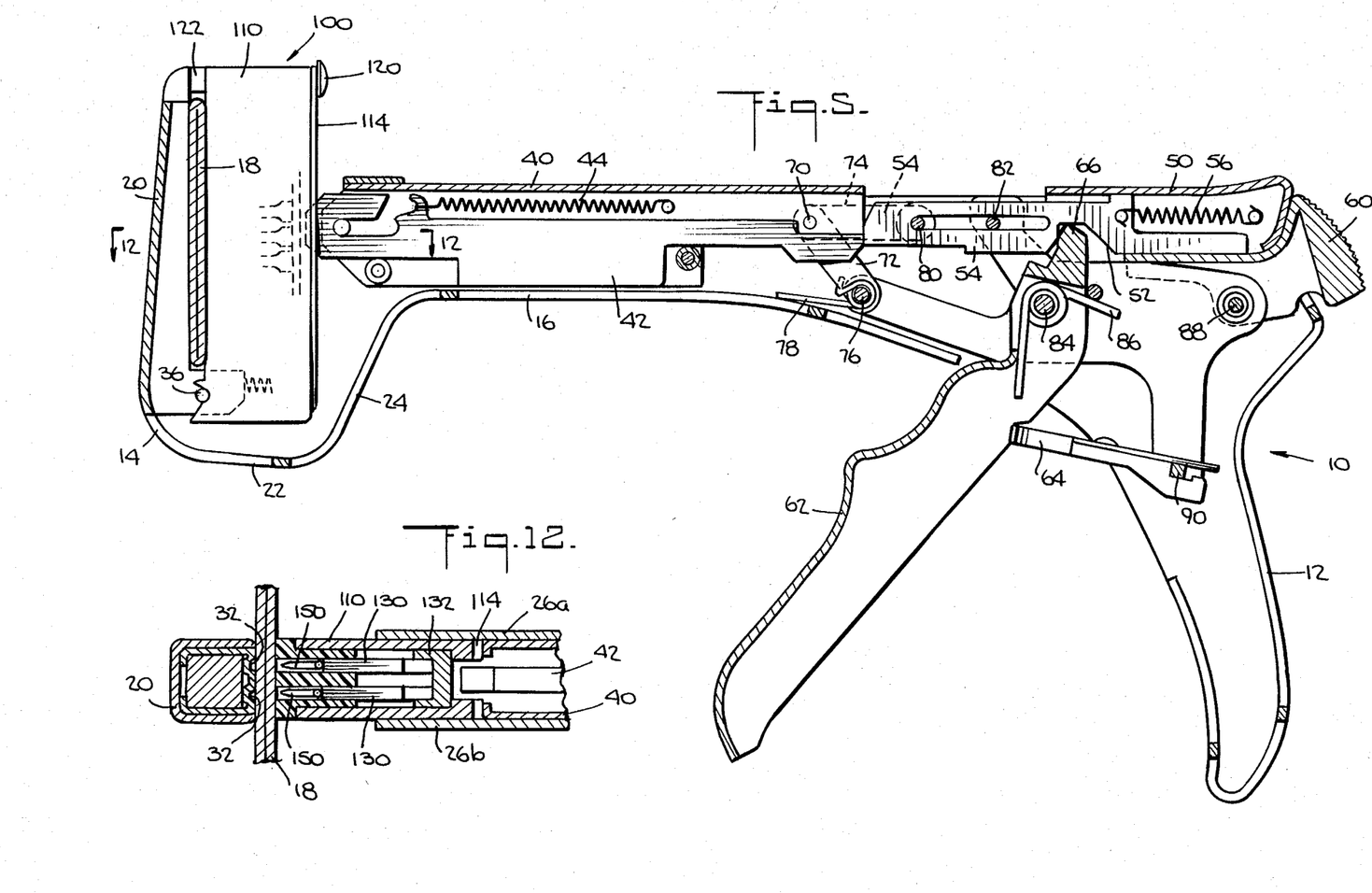
FIG. 12 is a sectional view taken along the line 12—12 in FIG. 5.
Figures 6, 10, 11:
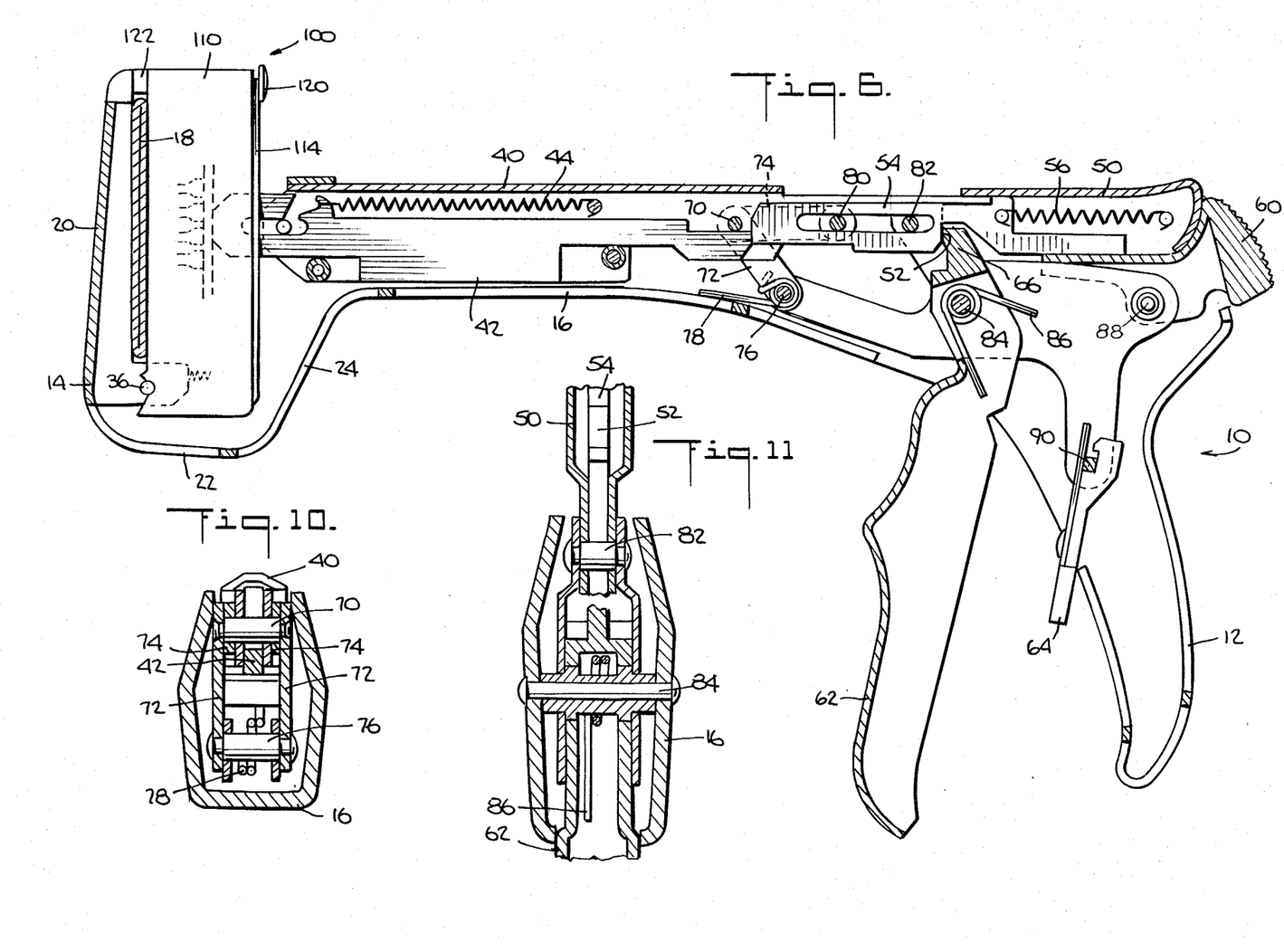

Trigger 62 is also pivotally mounted on actuator 10. A safety catch 64 may be provided for preventing inadvertent squeezing of trigger 62 toward handle 12. Safety catch 64 is shown in the "safety on" position in FIGS. 3–5, and in the "safety off" position in FIGS. 1, 2, and 6. The upper end of trigger 62 defines a lug 66 (FIG. 3), which, when clamp actuator 50 is pivoted down (FIG. 5), is received within a slot 52 in pusher bar 54 in clamp actuator 50. Pusher bar 54 is mounted for reciprocal motion in clamp actuator 50. Also, when clamp actuator 50 is pivoted down and clamping assembly 40 is therefore also pivoted down, pusher bar 54 is aligned with another pusher bar 42 which is mounted for reciprocal motion in clamping assembly 40. Accordingly, when pusher bars 42 and 54 are thus aligned, squeezing trigger 62 toward handle 12 drives pusher bars 42 and 54 in the distal direction. As will be discussed in more detail below, this causes the distal end of pusher bar 42 to enter fastener holding assembly 100 as shown in FIGS. 6 and 8, thereby driving the staples contained in that assembly toward anvil member 30.

When clamp actuator 50 is pivoted parallel to actuator 10, it locks in that position. Release 60 is pivotally mounted near the proximal end of actuator 10 to facilitate releasing that lock. Clamp actuator 50 is released and forced upward slightly when release 60 is manually depressed.

With reference to FIGS. 3–6, 10, and 11, some further details of actuator 10 are as follows. Pusher bar 42 is resiliently biased in the proximal direction by tension coil spring 44. Pin 70, which is the pivotal connection between links 72 and 74, is also the pivotal axis of clamping assembly 40. The distal end of link 72 is pivotally connected to the frame of actuator 10 by pin 76. Coil spring 78 urges link 72 to pivot clockwise about pin 76 as viewed in FIG. 3. The proximal end of link 74 is pivotally connected to clamp actuator 50 by pin 80. Clamp actuator 50 is pivotally connected to the frame of actuator 10 by pin 82. Pusher bar 54 is resiliently biased in the proximal direction by tension coil spring 56. The pivotal axis of trigger 62 is pin 84. Spring 86 urges trigger 62 to pivot about pin 84 in the clockwise direction as viewed in FIG. 3. The pivotal axis of release 60 is pin 88. Pin 90 is the pivotal axis of safety catch 64.

As best seen in FIG. 1, fastener holding assembly 100 includes an exterior housing 110. A plurality of U-shaped metal surgical staples 150 (FIG. 7) are disposed in two parallel rows of apertures 112 in the distal side of assembly 100. The staples in each row are offset from the staples in the other row to provide a staggered staple array. Leaf spring 114 is attached at one end near the bottom of housing 110. The major portion of leaf spring 114 extends along the proximal side of housing 110 and diverges from the housing toward the top of assembly 100. Pin 120 passes through an aperture near the top of assembly 100. The proximal end of pin 120 is captured by the upper end of spring 114.

Inside housing 110 each staple 150 has a pusher 130. All of pushers 130 are operated in unison by channel member 132. When fastener holding assembly 100 is mounted in actuator 10 and the tissue to be fastened is fully clamped as shown in FIG. 2, the distal end of pusher bar 42 can contact channel member 132 through slot 116 in spring 114 and aperture 118 in housing 110 (see FIGS. 7 and 8).

In operation, clamp actuator 50 is initially pivoted out as shown in FIG. 1 so that clamping assembly 40 can be pivoted parallel to shaft assembly 16 to place clamping assembly 40 in its proximally retracted position (see FIG. 3). Fastener holding assembly 100 is then dropped into actuator 10 between side plates 26. As described above and as shown in FIG. 3, the proximal end of pin 34 enters the distal end of aperture 140, but spring 142 keeps the lower portion of fastener holding assembly 100 spaced from the adjacent portion of anvil member 30. The tissue 18 to be fastened is positioned between anvil member 30 and fastener holding assembly 100.

The next step in the operation is to clamp the tissue between anvil member 30 and fastener holding assembly 100. This is accomplished by pivoting clamp actuator 50 parallel to shaft assembly 16, which causes clamping assembly 40 to translate in the distal direction. The distal end of clamping assembly 40 contacts leaf spring 114. This urges fastener holding assembly 100 in the distal direction and eventually flattens leaf spring 114 against the proximal side of housing 110. As leaf spring 114 is thus deflected, pin 120 moves distally relative to assembly 100 so that the distal end of pin 120 eventually projects from the distal side of housing 110 (see FIGS. 4, 7, and 8).

Figure 4:
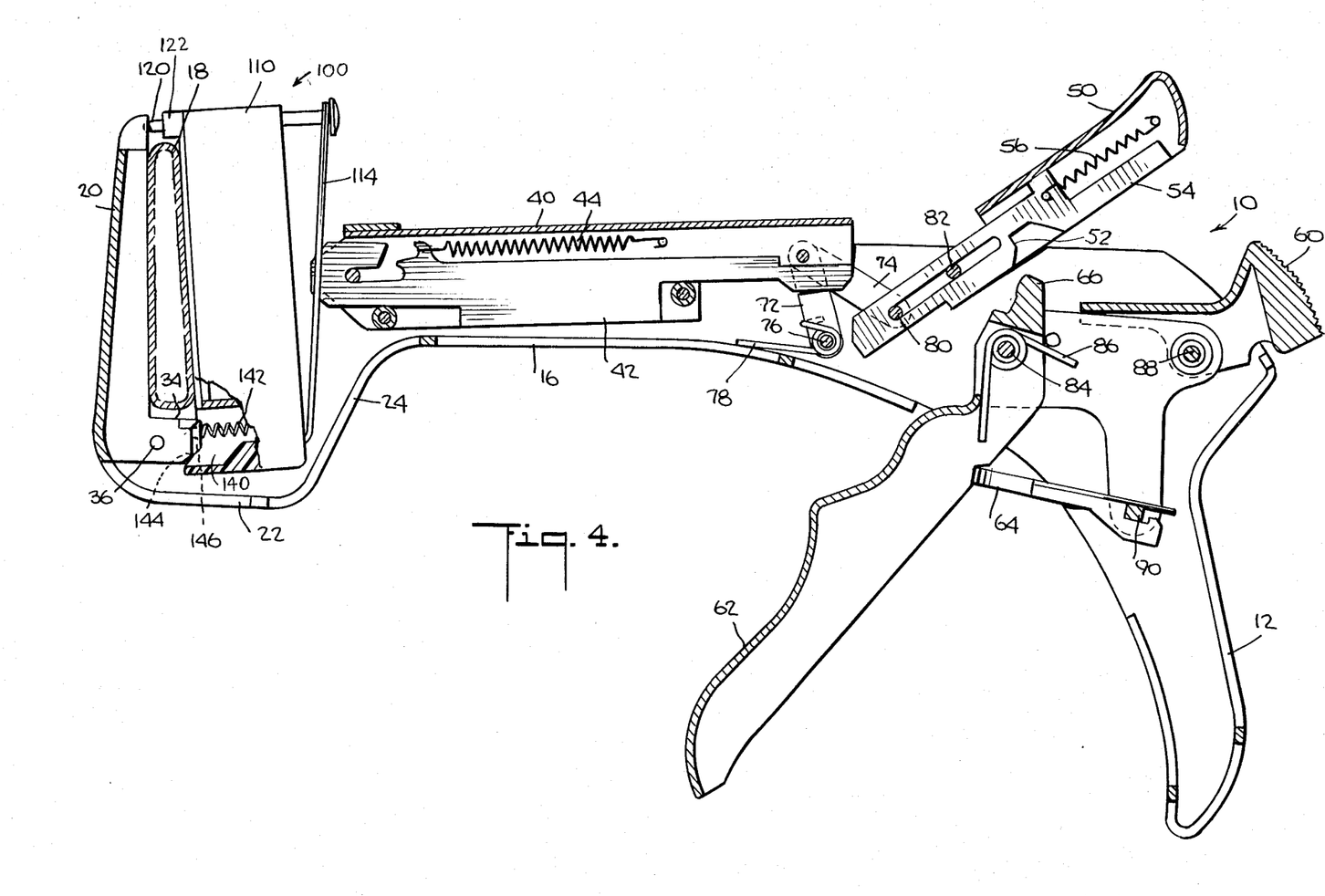

During the first portion of the distal motion of clamping assembly 40, fastener holding assembly 100 tends to pivot counterclockwise about the proximal end of pin 34 (see FIG. 4). This is because spring 142 resists distal motion of the lower portion of assembly 100, but the upper portion of assembly 100 is not similarly restrained. The presence of the proximal end of pin 34 in aperture 140 keeps fastener holding assembly 100 approximately aligned with anvil member 30. Plates 26 guide the motion of assembly 100. Because fastener holding assembly 100 pivots in this way, the initially open side of the tissue fastening site (i.e., the portion of that site adjacent pin 120) closes before full clamping pressure is applied to the tissue. Indeed, the distal end of pin 120 typically begins to enter aperture 38 in anvil member 30 as the top of fastener holding assembly 100 approaches anvil member 30 (see FIG. 4). Because the initially open side of the tissue fastening site is thus closed before full clamping pressure is applied to the tissue, the possible tendency of some of the tissue to squeeze out of the stapling site during clamping is substantially eliminated.

The above-described counterclockwise pivoting of fastener holding assembly 100 stops when the top spacer or seat portion 122 of fastener holding assembly 100 contacts anvil member 30. This occurs when the adjacent portions of fastener holding assembly 100 and anvil member 30 are a predetermined distance apart. Thereafter, further distal motion of clamping assembly 40 causes fastener holding assembly 100 to pivot in the opposite (clockwise) direction about the point of contact or bearing between that assembly and anvil member 30. This causes pin 34 to further penetrate aperture 140, thereby compressing spring 142. As clamping assembly 40 approaches the distal end of its travel, the ends of pin 36 enter V- or U-shaped yokes 144 on housing 110. The synclinal surfaces of yokes 144 guide the ends of pin 36 to the bottom of the V or U shapes which define semicylindrical bearing surfaces 146 for receiving the ends of pin 36 (see FIGS. 5, 7 and 8). When the ends of pin 36 contact bearing surfaces 146, a precision pivotal connection is formed between fastener holding assembly 100 and actuator 10. Assuming that spacer 122 first contacted anvil member 30 as described above, pin 36 seats against bearing surfaces 146 when fastener holding assembly 100 is parallel to anvil member 30. The precision pivotal connection including pin 36 and bearing surfaces 146 precisely aligns fastener holding assembly 100 with anvil member 30, thereby assuring that staples 150 will be properly crimped by the anvil. Proper alignment of anvil member 30 and fastener holding assembly 100 is further assured by the above-described extension of pin 120 from assembly 100 into aperture 38 in the anvil member. The tissue is now fully clamped and ready for fastening.

To fasten the tissue, safety catch 64 is pivoted down (FIG. 6) and trigger 62 is pivoted toward handle 12. This drives pusher bars 42 and 54 in the distal direction. The distal end of pusher bar 42 enters the proximal side of fastener holding assembly 100 and drives channel member 132 and pushers 130 in the distal direction. This drives all of staples 150 from apertures 112, through the clamped tissue, and against anvil member 30, which clinches the distal ends of all the staple legs to fasten the tissue (FIG. 8).

When the tissue has been fastened as described above, trigger 62 is released. This causes pusher bars 42 and 54 to retract in the proximal direction. Release 60 is then depressed to cause clamp actuator 50 to pivot up out of shaft assembly 16. This causes clamping assembly 40 to retract in the proximal direction, which allows fastener holding assembly 100 to pivot and translate away from anvil member 30. The fastened tissue is thus released and can be removed from the apparatus. The apparatus is readied for reuse by removing and discarding expended fastener holding assembly 100 and by reloading actuator 10 with a new fastener holding assembly 100. Between surgical procedures, actuator 10, which is assumed to be reusable, must be cleaned and sterilized. Cleaning is greatly facilitated by the fact that clamping assembly 40 and clamp actuator 50 both pivot out the remainder of the actuator assembly. Thus the entire actuator can be cleaned without any disassembly. Because fastener holding assemblies 100 are disposable, no cleaning, sterilization, or reloading of these assemblies is ever required.

Although the foregoing discussion of the operation of the apparatus assumes that fastener holding assembly 100 responds to distal motion of clamping assembly 40 by first pivoting counterclockwise and then pivoting clockwise as viewed in the drawing Figures, the motion of fastener holding assembly 100 typically also includes segments of translational motion. The actual motion of fastener holding assembly 100 may depend on the thickness and compressibility of the tissue. For example, although the foregoing discussion assumes that fastener holding assembly 100 first completely closes off the initially open side of the tissue fastening site, this is not necessarily always the case. If the tissue is relatively thick or hard, it may prevent the portion of fastener holding assembly 100 near pin 120 from contacting anvil member 30 until after the ends of pin 36 are fully seated against bearing surfaces 146. In that event, the final phase of the motion of fastener holding assembly 100 in response to distal extension of clamping assembly 40 will be pivotal motion (counterclockwise as viewed in FIGS. 3-6) about pin 36. The final position of fastener holding assembly 100 relative to anvil member 30 prior to fastening of the tissue is the same in any case.

Although in the particular embodiment shown in the drawing anvil member 30 is a fixed part of actuator 10, it will be understood that anvil member 30 could alternatively be removably mounted on the actuator. In that case, pin 34 is preferably integral with anvil member 30 so that fastener holding assembly 100 is always positioned accurately relative to anvil member 30 by the pivotal connection including pin 36. Similarly, although in the particular embodiment described herein the surgical fasteners applied by the apparatus are metal staples, it will be understood that other types of surgical fasteners can be applied by the apparatus of this invention. For example, surgical fasteners of the type shown in Noiles U.S. Pat. No. 4,060,089 can be applied. These are fasteners made up of two interlocking, typically plastic parts. If the present apparatus were adapted for applying surgical fasteners of this type, the fastener parts (i.e., the parts with prongs) would be driven from fastener holding assembly 100, and anvil member 30 would support the retainer members.

Those skilled in the art will appreciate that, although in the embodiment shown and described herein pin 34 is associated with anvil member 30, and aperture 140 is associated with fastener holding assembly 100, these elements could be reversed (i.e., the pin could be associated with the fastener holding assembly, and the aperture could be associated with the anvil member). Similarly, pin 36 could be associated with fastener holding element 100 and U- or V-shaped yokes 144 could be associated with anvil member 30.

It will be understood that the embodiments shown and described herein are only illustrative of the principles of this invention, and that various modifications can be made by those skilled in the art without departing from the scope and spirit of the invention. For example, two-part fasteners of plastic or plastic-like material can be substituted for metal staples as mentioned above.

We claim:

1. Apparatus for applying a plurality of surgical fasteners to body tissue in a longitudinal array comprising:
   a longitudinal anvil member for receiving the ends of a plurality of surgical fasteners driven parallel to a first axis which is perpendicular to the longitudinal axis of the anvil member;
   a first pin located adjacent a first end of the anvil member and having a longitudinal axis substantially parallel to the first axis;
   a longitudinal fastener holding assembly containing a plurality of surgical fasteners and adapted for driving the fasteners parallel to a second axis which is perpendicular to the longitudinal axis of the fastener holding assembly, the fastener holding assembly having a first aperture adjacent a first end of the fastener holding assembly for removably receiving the first pin, the first aperture permitting the fastener holding assembly to both translate relative to the anvil member substantially parallel to the first axis and pivot relative to the anvil member about axes which are mutually perpendicular to the first axis and the longitudinal axis of the anvil member.

2. The apparatus defined in claim 1 further comprising:
   clamping means mounted relative to the anvil member for applying clamping force to the side of the fastener holding assembly which is remote from the anvil member, the clamping force being applied along a second axis which is parallel to the first axis and which, when the first pin is disposed in the first aperture, is intermediate the first aperture and the opposite second end of the fastener holding assembly.

3. The apparatus defined in claim 2 further comprising:
   spring means disposed adjacent the first aperture for resiliently biasing the adjacent portions of the anvil member and the fastener holding assembly apart when the pin is disposed in the first aperture.

4. The apparatus defined in claim 1 further comprising:
   first seat means disposed adjacent the first pin for stopping translation of the fastener holding assembly toward the anvil member when the adjacent portions of the anvil member and the fastener holding assembly are a first predetermined distance apart; and
   second seat means disposed adjacent the second end of the anvil member for stopping translation of the fastener holding assembly toward the anvil member when the adjacent portions of the anvil member and the fastener holding assembly are a second predetermined distance apart.

5. The apparatus defined in claim 4 wherein the first seat means comprises:
   a second pin perpendicular to the first pin and mounted relative to one of the anvil member and the fastener holding assembly; and
   yoke means mounted relative to the other of the anvil member and the fastener holding assembly and opening toward said one of the anvil member and the fastener holding assembly, the pin seating in the bottom of the yoke means when the adjacent portions of the anvil member and the fastener holding assembly are a first predetermined distance apart.

6. The apparatus defined in claim 5 wherein the yoke means comprises:
synclinal side surfaces for guiding the second pin toward the bottom of the yoke means.

7. The apparatus defined in claim 6 wherein the second pin and the bottom of the yoke means cooperate to form a pivotal connection between the anvil member and the fastener holding assembly when the second pin is seated in the bottom of the yoke means.

8. The apparatus defined in claim 1 further comprising:
a third pin mounted on one of the anvil member and the fastener holding assembly adjacent the second end of the fastener holding assembly, the third pin being substantially perpendicular to the first axis; and
a second aperture located in the other of the anvil member and the fastener holding assembly adjacent the second end of the fastener holding assembly for removably receiving the third pin when the fastener holding assembly translates toward the anvil member to align the adjacent portions of the anvil member and the fastener holding assembly.

9. The apparatus defined in claim 1 further comprising:
frame means including a U-shaped portion having first and second legs connected together by a base, the anvil member being mounted on the first leg with the first pin being adjacent the base, and the second leg including laterally spaced side members between which the fastener assembly can be inserted, the side members guiding the fastener holding assembly toward the anvil member so that the first pin enters the first aperture.

10. The apparatus defined in claim 9 further comprising:
clamping means mounted on the frame means for applying clamping force to the side of the fastener holding assembly which is remote from the anvil member, the clamping force being applied along a second axis which is parallel to the first axis and which, when the first pin is disposed in the first aperture, is intermediate the first aperture and the opposite second end of the fastener holding assembly.

11. In apparatus for applying a plurality of surgical fasteners to body tissue in a longitudinal array, the apparatus including a longitudinal anvil member and a longitudinal fastener holding assembly, improved means for mounting the anvil member and fastener holding assembly in parallel, spaced relationship to one another comprising:
first and second mounting means at respective opposite ends of the anvil member;
third and fourth mounting means at respective opposite ends of the fastener holding assembly, the first and third mounting means being separable but cooperable with one another to form a pivotal bearing between the anvil member and the fastener holding assembly, the pivotal axis of the bearing being perpendicular to the plane defined by the parallel, spaced, longitudinal axes of the anvil member and the fastener holding assembly, the pivotal bearing being open on one circumferential side so that the anvil member and the fastener holding assembly are movable away from one another along a translational axis mutually perpendicular to their longitudinal axes and to the pivotal axis of the bearing, one of the first and third mounting means including a pin substantially parallel to the translational axis and the other of the first and third mounting means including an aperture having a cross section larger than the cross section of the pin for receiving the pin and guiding the parts of the pivotal bearing into engagement with one another when the anvil member and the fastener holding assembly are moved toward one another along the translational axis, and the second and fourth mounting means being separable but cooperable with one another to align the adjacent ends of the anvil member and the fastener holding assembly.

12. In apparatus for applying a plurality of surgical fasteners to body tissue in a longitudinal array, the apparatus including a longitudinal anvil member and a longitudinal fastener holding assembly, improved means for mounting the anvil member and fastener holding assembly in parallel, spaced relationship to one another comprising:
first and second mounting means at respective opposite ends of the anvil member;
third and fourth mounting means at respective opposite ends of the fastener holding assembly, the first and third mounting means being separable but cooperable with one another to form a pivotal bearing between the anvil member and the fastener holding assembly, the pivotal axis of the bearing being perpendicular to the plane defined by the parallel, spaced, longitudinal axes of the anvil member and the fastener holding assembly, the pivotal bearing being open on one circumferential side so that the anvil member and the fastener holding assembly are movable away from one another along a translational axis mutually perpendicular to their longitudinal axes and to the pivotal axis of the bearing, one of the first and third mounting means comprising a pin, the longitudinal axis of which is the pivotal axis, and the other of the first and third mounting means comprising a U- or V-shaped structure for engaging a portion of the side surface of the pin in the base of the U or V to provide the pivotal bearing, the first and third mounting means further including means for guiding the parts of the pivotal bearing into engagement with one another when the anvil member and the fastener holding assembly are moved toward one another along the translational axis, and the second and fourth mounting means being separable but cooperable with one another to align the adjacent ends of the anvil member and the fastener holding assembly.

13. The apparatus defined in claim 12 wherein the first and third mounting means include spring means for resiliently biasing the parts of the pivotal bearing apart parallel to the translational axis.

14. In apparatus for applying a plurality of surgical fasteners to body tissue in a longitudinal array, the apparatus including a longitudinal anvil member and a longitudinal fastener holding assembly, improved means for mounting the anvil member and fastener holding assembly in parallel, spaced relationship to one another comprising:
first and second mounting means at respective opposite ends of the anvil member;
third and fourth mounting means at respective opposite ends of the fastener holding assembly, the first and third mounting means being separable but cooperable with one another to form a pivotal bearing between the anvil member and the fastner holding assembly, the pivotal axis of the bearing being perpendicular to the plane defined by the parallel, spaced, longitudinal axes of the anvil member and the fastener holding assembly, the pivotal bearing being open on one circumferential side so that the anvil member and the fastener holding assembly are movable away from one another along a translational axis mutually perpendicular to their longitudinal axes and to the pivotal axis of the bearing, the first and third mounting means further including means for guiding the parts of the pivotal bearing into engagement with one another when the anvil member and the fastener holding assembly are moved toward one another along the translational axis, and the second and fourth mounting means being separable but cooperable with one another to align the adjacent ends of the anvil member and the fastener holding assembly, wherein one of the second and fourth mounting means comprises a pin substantially parallel to the translational axis, and wherein the other of the second and fourth mounting means comprises an aperture for receiving an end portion of the pin.

15. The apparatus defined in claim 14 wherein the pin is mounted for reciprocal motion parallel to the translational axis.

16. Apparatus for applying a plurality of surgical fasteners to body tissue in a longitudinal array comprising:
a frame having a U-shaped portion for receiving the tissue to be fastened between the legs of the U;
a longitudinal anvil member mounted on one leg of the U;
a longitudinal fastener holding assembly;
means for removably mounting the fastener holding assembly adjacent the second leg of the U and the anvil member so that the fastener holding assembly is both linearly and pivotally movable toward the anvil member, said means including (1) a first pin mounted on one of the frame and the fastener holding assembly and having a longitudinal axis perpendicular to the plane defined by the legs of the U, and (2) a U- or V-shaped structure mounted on the other of the frame and the fastener holding assembly for receiving a portion of the side surface of the second pin adjacent the base of the U- or V-shaped structure to provide a pivotal connection between the fastener holding assembly and the remainder of the apparatus; and
actuator means mounted on the frame for urging the longitudinal fastener holding assembly toward the anvil member.

17. The apparatus defined in claim 16 wherein the means for removably mounting the fastener holding assembly further comprises:
a second pin mounted on one of the frame and the fastener holding assembly and having a longitudinal axis parallel to the plane defined by the legs of the U and perpendicular to the longitudinal axis of the anvil member; and
an aperture in the other of the frame and the fastener holding assembly for receiving the second pin.

18. The apparatus defined in claim 17 wherein the transverse dimension of the aperture parallel to the longitudinal axis of the anvil member is substantially greater than the corresponding dimension of the second pin to facilitate pivoting of the fastener holding assembly toward the anvil member.

19. The apparatus defined in claim 18 wherein the means for removably mounting the fastener holding assembly further comprises spring means for resiliently biasing the fastener holding assembly away from the anvil member.

20. The apparatus defined in claim 18 wherein the first and second pins are both located adjacent the base of the U-shaped frame, and wherein the means for removably mounting the fastener holding assembly further comprises means located adjacent the normally open side of the U-shaped frame for mutually aligning the adjacent portions of the anvil member and the fastener holding assembly.

21. The apparatus defined in claim 20 wherein the means located adjacent the normally open side of the U-shaped frame comprises:
a third pin substantially parallel to the second pin and mounted on one of the fastener holding assembly and the leg of the frame on which the anvil member is mounted; and
an aperture for receiving the third pin and mounted on the other of the fastener holding assembly and the leg of the frame on which the anvil member is mounted.

22. The apparatus defined in claim 21 wherein the third pin is mounted for reciprocal motion parallel to its longitudinal axis.

23. The apparatus defined in claim 20 wherein the actuator means comprises means for applying force to the fastener holding assembly along an actuator axis which is parallel to the longitudinal axis of the second pin and intermediate the first pin and the means located adjacent the normally open side of the U-shaped frame.

24. A surgical fastener cartridge for use in surgical fastener applying apparatus including frame means having a U-shaped portion, an anvil member mounted on a first leg of the U, and first cartridge mounting means disposed adjacent the base of the U and including a pin perpendicular to the plane defined by the first and second legs of the U, the cartridge comprising:
a longitudinal housing containing a plurality of surgical fasteners and means for driving the surgical fasteners from the housing parallel to a first axis which is perpendicular to the longitudinal axis of the housing;
second cartridge mounting means disposed adjacent a first end of the housing for releasably engaging the first cartridge mounting means when the cartridge is positioned relative to the second leg of the U, the first and second cartridge mounting means cooperating to allow the adjacent portion of the fastener holding assembly to translate toward the anvil member and also allowing the fastener holding assembly to pivot toward the anvil member, the second cartridge mounting means including yoke means for contacting the pin and forming a pivotal connection between the cartridge and the frame means, the pivotal axis of the pivotal connection being the longitudinal axis of the pin.

25. A surgical fastener cartridge for use in surgical fastener applying apparatus including frame means having a U-shaped portion, an anvil member mounted on a first leg of the U, and first cartridge mounting means disposed adjacent the base of the U and including a first pin parallel to the plane defined by the first and second legs of the U and perpendicular to the first leg of the U, the cartridge comprising:

a longitudinal housing containing a plurality of surgical fasteners and means for driving the surgical fasteners from the housing parallel to a first axis which is perpendicular to the longitudinal axis of the housing;

second cartridge mounting means disposed adjacent a first end of the housing for releasably engaging the first cartridge mounting means when the cartridge is positioned relative to the second leg of the U, the first and second cartridge mounting means cooperating to allow the adjacent portion of the fastener holding assembly to translate toward the anvil member and also allowing the fastener holding assembly to pivot toward the anvil member, the second cartridge mounting means including a first aperture in the housing for receiving the first pin.

26. The apparatus defined in claim 25 wherein the first cartridge mounting means further includes a second pin perpendicular to the plane defined by the first and second legs of the U, and wherein the second cartridge mounting means further comprises:

yoke means for contacting the second pin and forming a pivotal connection between the cartridge and the frame means, the pivotal axis of the pivotal connection being the longitudinal axis of the second pin.

27. The apparatus defined in claim 25 wherein the second cartridge mounting means comprises:

spring menas for resiliently biasing the adjacent portions of the cartridge and the anvil member apart parallel to the plane defined by the first and second legs of the U.

28. The apparatus defined in claim 25 wherein the fastener applying apparatus further includes first alignment means disposed adjacent the end of the first leg of the U remote from the base, and wherein the cartridge further comprises:

second alignment means disposed adjacent the second end of the housing for releasably engaging the first alignment means when the cartridge is disposed adjacent the anvil member to align the adjacent portions of the anvil member and the cartridge.

29. The apparatus defined in claim 28 wherein the first alignment means includes a second aperture, and wherein the second alignment means comprises:

a third pin substantially parallel to the first pin.

30. The apparatus defined in claim 29 wherein the cartridge further comprises:

means for mounting the third pin for reciprocal motion parallel to its longitudinal axis; and means for automatically extending the third pin from the housing toward the first leg of the U only when the cartridge is moved toward the anvil member.

* * * * *